US008637571B2

(12) United States Patent
Hughes et al.

(10) Patent No.: US 8,637,571 B2
(45) Date of Patent: *Jan. 28, 2014

(54) COMPOSITIONS AND METHODS FOR THE INTRAOCULAR TRANSPORT OF THERAPEUTIC AGENTS

(75) Inventors: Patrick M. Hughes, Aliso Viejo, CA (US); Orest Olejnik, Coto de Caza, CA (US); Joan-En Chang-Lin, Tustin, CA (US)

(73) Assignee: Allergan, Inc., Irvine, CA (US)

( * ) Notice: Subject to any disclaimer, the term of this patent is extended or adjusted under 35 U.S.C. 154(b) by 203 days.

This patent is subject to a terminal disclaimer.

(21) Appl. No.: 12/730,102

(22) Filed: Mar. 23, 2010

(65) Prior Publication Data

US 2010/0222587 A1    Sep. 2, 2010

Related U.S. Application Data

(63) Continuation of application No. 11/521,872, filed on Sep. 15, 2006, now Pat. No. 7,714,024.

(60) Provisional application No. 60/717,946, filed on Sep. 16, 2005.

(51) Int. Cl.
*A61K 31/201*    (2006.01)
*A61K 38/04*    (2006.01)

(52) U.S. Cl.
USPC ............ 514/559; 514/313; 514/530; 514/573

(58) Field of Classification Search
USPC .......................................... 514/392, 530, 559
See application file for complete search history.

(56) References Cited

U.S. PATENT DOCUMENTS

| | | | |
|---|---|---|---|
| 5,443,505 A | 8/1995 | Wong | |
| 5,632,984 A | 5/1997 | Wong | |
| 5,766,242 A | 6/1998 | Wong | |
| 5,824,072 A | 10/1998 | Wong | |
| 5,869,079 A | 2/1999 | Wong | |
| 6,331,313 B1 | 12/2001 | Wong | |
| 6,369,116 B1 | 4/2002 | Wong | |
| 6,699,493 B2 | 3/2004 | Wong | |
| 6,726,918 B1 | 4/2004 | Wong | |
| 7,714,024 B2 | 5/2010 | Hughes et al. | |
| 7,931,909 B2 | 4/2011 | Hughes et al. | |
| 2002/0010202 A1* | 1/2002 | Garst ........................... | 514/392 |
| 2004/0198829 A1 | 10/2004 | Sponsel et al. | |
| 2005/0043246 A1 | 2/2005 | Mitra et al. | |
| 2008/0139652 A1* | 6/2008 | Sakai et al. ................... | 514/559 |

FOREIGN PATENT DOCUMENTS

| | | |
|---|---|---|
| WO | WO 03/048190 | 6/2003 |
| WO | 03/077952 | 9/2003 |
| WO | 2005/107705 | 11/2005 |
| WO | 2005/110362 | 11/2005 |
| WO | 2005/110367 | 11/2005 |
| WO | 2005/110368 | 11/2005 |
| WO | 2006/122165 | 11/2006 |

OTHER PUBLICATIONS

Alm A, Törnquist P. *Lactate transport through the blood-retinal and the blood-brain barrier in rats.* Ophthalmic Res. 17 (1985) 181-184.

Atluri H, Anand BS, Patel J, Mitra AK., *Mechanism of a model dipeptide transport across blood-ocular barriers following systemic administration.* Exp Eye Res. 78(4) Apr. 2004 815-22.

Aukunuru JV, Sunkara G, Bandi N, Thoreson WB, Kompella UB. *Expression of multidrug resistance-associated protein (MRP) in human retinal pigment epithelial cells and its interaction with BAPSG, a novel aldose reductase inhibitor.* Pharm Res. 18(5) (2001) 565-72.

Basu SK, Haworth IS, Bolger MB, Lee VHL. *Proton-driven dipeptide uptake in primary cultured rabbit conjunctival epithelial cells.* Invest Ophthalmol Vis Sci. 39 (1998) 2365-2373.

Berger UV, Hediger MA., *Distribution of peptide transporter PEPT2 mRNA in the rat nervous system.* Anat Embryol (Berl). 199(5) May 1999 439-49.

Bergersen L, Johannsson E, Veruki ML, Nagelhus EA, Halestrap A, Sejersted OM, Ottersen OP. *Cellular and subcellular expression of monocarboxylate transporters in the pigment epithelium and retina of the rat.* Neuroscience. 90(1) (1999) 319-31.

Blazynski C. *The accumulation of [3H]phenylisopropyl adenosine ([3H]PIA) and [3H]adenosine into rabbit retinal neurons is inhibited by nitrobenzylthioinosine (NBI).* Neurosci Lett. 121(1-2) (1991) 1-4.

Brecha NC, Weigmann C. *Expression of GAT-1, a high-affinity gamma-aminobutyric acid plasma membrane transporter in the rat retina.* J Comp Neurol. 345(4) (1994) 602-11.

Chancy CD, Kekuda R, Huang W, Prasad PD, Kuhnel JM, Sirotnak FM, Roon P, Ganapathy V, Smith SB. *Expression and differential polarization of the reduced-folate transporter-1 and the folate receptor α in mammalian retinal pigment epithelium.* J Biol Chem. 275(27) (2000) 20676-20684.

Cunha-Vaz, J.G., *The blood-ocular barriers: past, present, and future,* Documenta Ophthalmologica, Advances in Ophthalmology, 1997, No. 93, No. 1-2, pp. 149-157.

Duyvuri, S., et al., *Drug delivery to the retina: challenges and opportunities,* Expert Opinion on Biological Therapy, 2003, vol. 3, No. 1, pp. 46-56.

Gao G, Wenzel A, Grimm C, Vavricka SR, Benke D, Meier PJ, Reme CE, "Localization of organic anion transport protein 2 in the apical region of rat retinal pigment epithelium". Invest Ophthalmol Vis Sci. 43(2) (2002) 510-4.

George RI, Huang W. Naggar HA, Smith SB, Ganapathy V., "Transport of N-acetylaspartate via murine sodium/dicarboxylate cotransporter NaDC3 and expression of this transporter and aspartoacylase II in ocular tissues in mouse". Biochim Biophys Acta. 1690(1)(2004)63-9.

Gerhart DZ, Leino RI, Drewes LR, "Distribution of monocarboxylate transporters MCT1 and MCT2 in rat retina". Neuroscience. 92(1) (1999) 367-75.

(Continued)

*Primary Examiner* — Michael G Hartley
*Assistant Examiner* — Jagadishwar Samala
(74) *Attorney, Agent, or Firm* — Laura L. Wine; Joel German

(57) ABSTRACT

Membrane transporter-targeted therapeutic agents and methods of making and using the same.

5 Claims, No Drawings

(56) References Cited

OTHER PUBLICATIONS

Gherzi R, Melioli G, De Luca M, D'Agostino A, Guastella M, Traverso CE, D'Anna F, Franzi AT, Cancedda R. *High expression levels of the "erythroid/brain" type glucose transporter (GLUT1) in the basal cells of human eye conjunctiva and oral mucosa reconstituted in culture.* Exp Cell Res. 195(1) (1991) 230-6.

Greenwood J. *Characterization of a rat retinal endothelial cell culture and the expression of P-glycoprotein in brain and retinal endothelium in vitro.* J Neuroimmunol. 39(1-2) (1992) 123-32.

Gu S, Roderick HL, Camacho P, Jiang JX., *Characterization of an N-system amino acid transporter expressed in retina and its involvement in glutamine transport.,* J Biol Chem. 276(26) Jun. 29, 2001 24137-44.

Hamann S, Kiilgaard JF, Ia Cour M, Prause JU, Zeuthen T. *Cotransport of H+, lactate, and H2O in porcine retinal pigment epithelial cells.* Exp Eye Res. 76(4) (2003) 493-504.

Han YH, Sweet DH, Hu DN, Pritchard JB. *Characterization of a novel cationic drug transporter in human retinal pigment epithelial cells.* J Pharmacol Exp Ther. 296(2) (2001) 450-7.

Han et al., *Regulation of aquaporin-4 water channels by phorbol ester-dependent protein phosphorylation,* Journal of Biological Chemistry, American Society of Biolochemical Biologists, Birmingham, U.S., 1998, vol. 273, No. 11, pp. 6001-6004.

Harik SI, Kalaria RN, Whitney PM, Anderson L, Lundahl P, Ledbetter SR, Perry G. *Glucose transporters are abundant in cells with "occluding" junctions at the blood-eye barriers.* Proc Natl Acad Sci USA. 87(11) (1990) 4261-4.

Honda S, Yamamoto M, Saito N. *Immunocytochemical localization of three subtypes of GABA transporter in rat retina.* Brain Res Mol Brain Res. 33(2) (1995) 319-25.

Horibe Y, Hosoya K, Kim KJ, Lee VH. *Carrier-mediated transport of monocarboxylate drugs in the pigmented rabbit conjunctiva.* Invest Ophthalmol Vis Sci. 39(8) (1998) 1436-43.

Horibe Y, Hosoya K, Kim KJ, Lee VH. *Kinetic evidence for Na(+)-glucose co-transport in the pigmented rabbit conjunctiva.* Curr Eye Res. 16(10) (1997) 1050-5.

Horibe Y, Hosoya K, Kim KJ, Ogiso T, Lee VH. *Polar solute transport across the pigmented rabbit conjunctiva: Size dependence and the influence of 8-bromo cyclic adenosine monophosphate.* Pharm Res. 14(9) (1997) 1246-1251.

Hosoya K, Horibe Y, Kim KJ, Lee VH. *Nucleoside transport mechanisms in the pigmented rabbit conjunctiva.* Invest Ophthalmol Vis Sci. 39(2) (1998) 372-7.

Hosoya K, Horibe Y, Kim KJ, Lee VH., *Na(+)-dependent L-arginine transport in the pigmented rabbit conjunctiva.* Exp Eye Res. 65(4) Oct. 1997 547-53.

Hosoya K, Kompella UB, Kim KJ, Lee VH. *Contribution of Na(+)-glucose cotransport to the short-circuit current in the pigmented rabbit conjunctiva.* Curr Eye Res. 15(4) (1996) 447-51.

Hosoya K, Kondo T, Tomi M, Takanaga H, Ohtsuki S, Terasaki T. *MCT1-mediated transport of L-lactic acid at the inner blood-retinal barrier: a possible route for delivery of monocarboxylic acid drugs to the retina.* Pharm Res. 18(12) (2001) 1669-76.

Hu M, Bruun A, Ehinger B. *Expression of GABA transporter subtypes (GAT1, GAT3) in the adult rabbit retina.* Acta Ophthalmol Scand. 77(3) (1999) 255-60.

Inoue K, Sakaitani M, Shimada S, Tohyama M., *Cloning and expression of a bovine glutamate transporter.* Brain Res Mol Brain Res. 28(2) Feb. 1995 343-8.

Ito A, Yamaguchi K, Onogawa T, Unno M, Suzuki T, Nishio T, Suzuki T, Sasano H, Abe T, Tamai M. *Distribution of organic anion-transporting polypeptide 2 (oatp2) and oatp3 in the rat retina.* Invest Ophthalmol Vis Sci. 43(3) (2002) 858-63.

Ito A, Yamaguchi K, Tomita H, Suzuki T, Onogawa T, Sato T, Mizutamari H, Mikkaichi T, Nishio T, Suzuki T, Unno M, Sasano H, Abe T, Tamai M. *Distribution of rat organic anion transporting polypeptide-E (oatp-E) in the rat eye.* Invest Ophthalmol Vis Sci. 44(11) (2003) 4877-4884.

Kennedy BG, Mangini NJ. *P-glycoprotein expression in human retinal pigment epithelium.* Mol Vis. 11(8) (2002) 422-30.

Kenyon I, Yu K, La Cour M, Miller SS. *Lactate transport mechanisms at apical and basolateral membranes of bovine retinal pigment epithelium.* Am J Physiol. 267 (1994) C1561-C1573.

Kim In-Beom et al., *Immunocytochemical localization of Aquaporin 1 in the rat retina,* Neuroscience Letters, Mar. 6, 1998, vol. 244, No. 1, pp. 52-54.

Knott RM, Robertson M, Forrester JV. *Regulation of glucose transporter (GLUT 3) and aldose reductase mRNA in bovine retinal endothelial cells and retinal pericytes in high glucose and high galactose culture.* Diabetologia. 36(9) (1993) 808-12.

Knott RM, Robertson M, Muckersie E, Folefac VA, Fairhurst FE, Wileman SM, Forrester JV. *A model system for the study of human retinal angiogenesis: activation of monocytes and endothelial cells and the association with the expression of the monocarboxylate transporter type 1 (MCT-1).* Diabetologia. 42(7) (1999) 870-7.

Kompella UB, Kim KJ, Shiue MH, Lee VH., *Possible existence of Na(+)-coupled amino acid transport in the pigmented rabbit conjunctiva.* 57(15) Life Sci. 1995 1427-31.

Majumdar S, Macha S, Pal D, Mitra AK. *Mechanism of ganciclovir uptake by rabbit retina and human retinal pigmented epithelium cell line ARPE-19.* Curr Eye Res. 29(2-3) (2004) 127-36.

Mantych GJ, Hageman GS, Devaskar SU. *Characterization of glucose transporter isoforms in the adult and developing human eye.* Endocrinology. 133(2) (1993) 600-7.

Ocheltree SM, Keep RF, Shen H, Yang D, Hughes BA, Smith DE. *Preliminary investigation into the expression of proton-coupled oligopeptide transporters in neural retina and retinal pigment epithelium (RPE): lack of functional activity in RPE plasma membranes.* Pharm Res. 20(9) (2003) 1364-72.

Patil RV, Saito I, Yang X, Wax MB. *Expression of aquaporins in the rat ocular tissue.* Exp Eye Res. 64 (1997) 203-209.

Peterson WM, Miller SS. *Identification and functional characterization of a dual GABA/taurine transporter in the bullfrog retinal pigment epithelium.* J Gen Physiol. 106(6) (1995) 1089-122.

Philp NJ, Wang D, Yoon H, Hjelmeland LM. *Polarized expression of monocarboxylate transporters in human retinal pigment epithelium and ARPE-19 cells.* Invest Ophthalmol Vis Sci. 44(4) (2003) 1716-21.

Philp NJ, Yoon H, Grollman EF. *Monocarboxylate transporter MCT1 is located in the apical membrane and MCT3 in the basal membrane of rat RPE.* Am J Physiol. 274(6 Pt 2) (1998) R1824-8.

Pignataro L, Sitaramayya A, Finnemann SC, Sarthy VP. *Nonsynaptic localization of the excitatory amino acid transporter 4 in photoreceptors.* Mol Cell Neurosci. 28(3) (2005) 440-51.

Rajan PD, Kekuda R, Chancy CD, Huang W, Ganapathy V, Smith SB. *Expression of the extraneuronal monoamine transporter in RPE and neural retina.* Curr Eye Res. 20(3) (2000) 195-204.

Rauen T., *Diversity of glutamate transporter expression and function in the mammalian retina.* Amino Acids. 19(1) 2000 53-62.

Ruiz M, Egal H, Sarthy V, Qian X, Sarkar HK. *Cloning, expression, and localization of a mouse retinal gamma-aminobutyric acid transporter.* Invest Ophthalmol Vis Sci. 35(12) (1994) 4039-48.

Saha P, Yang JJ, Lee VH. *Existence of a p-glycoprotein drug efflux pump in cultured rabbit conjunctival epithelial cells.* Invest Ophthalmol Vis Sci. 39(7) (1998) 1221-6.

Shi XP, Candia OA. *Active sodium and chloride transport across the isolated rabbit conjunctiva.* Curr Eye Res. 14(10) (1995) 927-35.

Steuer H, Jaworski A, Elger B, Kaussmann M, Keldenich J, Schneider H, Stoll D, Schlosshauer B. *Functional characterization and comparison of the outer blood-retina barrier and the blood-brain barrier.* Invest Ophthalmol Vis Sci. 46(3) (2005) 1047-1053.

Tenckhoff S, Hollborn M, Kohen L, Wolf S, Wiedemann P, Bringmann A. *Diversity of aquaporin mRNA expressed by rat and human retinas.* Neuroreport. 16(1) (2005) 53-6.

To CH, Cheung KK, Chiu SH, Lai HM, Lung KS. *The saturation characteristics of glucose transport in bovine retinal pigment epithelium.* Yan Ke Xue Bao. 14(3) (1998) 126-9.

Tornquist P, Alm A., *Carrier-mediated transport of amino acids through the blood-retinal and the blood-brain barriers.* Graefes Arch Clin Exp Ophthalmol. 224(1) 1986 21-5.

(56) References Cited

OTHER PUBLICATIONS

Tsukamoto H, Mishima HK, Kurokawa T, Kiuchi Y, Sato E, Ishibashi S. *Isoforms of glucose transporter in the iris-ciliary body. Jpn J Ophthalmol.* 39(3) (1995) 242-7.

Ueda H, Horibe Y, Kim KJ, Lee VH., *Functional characterization of organic cation drug transport in the pigmented rabbit conjunctiva. Invest Ophthalmol Vis Sci.* 41 (3) (2000) 870-6.

Walters HA, Craddock AL, Fusegawa H, Willingham MC, Dawson PA., *Expression, transport properties, and chromosomal location of organic anion transporter subtype 3. Am J Physiol Gastrointest Liver Physiol.* 279(6) Dec. 2000 G1188-200.

Watanabe T, Mio Y, Hoshino FB, Nagamatsu S, Kirosawa K, Nakahara K. *GLUT2 expression in the rat retina: location at the apical ends of Muller cells. Brain Res.* 655(1-2) (1994) 128-34.

Williams EF, Ezeonu I, Dutt K. *Nucleoside transport sites in a cultured human retinal cell line established by SV-40 T antigen gene. Curr Eye Res.* 13(2) (1994) 109-18.

Zhao JW, Du JL, Li JS, Yang XL. *Expression of GABA transporters on bullfrog retinal Muller cells. Glia.* 31(2) (2000) 104-17.

Zhao JW, Yang XL., *Glutamate transporter EAAC1 is expressed on Muller cells of lower vertebrate retinas. J Neurosci Res.* 66(1) Oct. 1, 2001 89-95.

Merkli A et al: "Use of Insoluble Biodegradable Polymers in Ophthalmic Systems for the Sustained Release of Drugs" European Journal of Pharmaceutics and Biopharmaceutics, Elsevier Science Publishers B.V., Amsterdam, NL, vol. 41, No. 5, Oct. 1, 1995, pp. 271-283.

* cited by examiner

COMPOSITIONS AND METHODS FOR THE INTRAOCULAR TRANSPORT OF THERAPEUTIC AGENTS

CROSS REFERENCE

This is a continuation U.S. application Ser. No. 11/521,872, filed Sep. 15, 2006, which claims the benefit of U.S. Provisional Patent Application No. 60/717,946, filed Sep. 16, 2005, both incorporated entirely by reference.

BACKGROUND

The mammalian eye is a complex organ comprising an outer covering including the sclera (the tough white portion of the exterior of the eye) and the cornea, the clear outer portion covering the pupil and iris. In a medial cross section, from anterior to posterior, the eye comprises features including, without limitation: the cornea, the anterior chamber (a hollow feature filled with a watery clear fluid called the aqueous humor and bounded by the cornea in the front and the lens in the posterior direction), the iris (a curtain-like feature that can open and close in response to ambient light) the lens, the posterior chamber (filled with a viscous fluid called the vitreous humor), the retina (the innermost coating of the back of the eye comprised of light-sensitive neurons), the choroid (and intermediate layer providing blood vessels to the cells of the eye), and the sclera. The posterior chamber comprises approximately ⅔ of the inner volume of the eye, while the anterior chamber and its associated features (lens, iris etc.) comprise about ⅓ of the eye's volume.

The delivery of therapeutic agents to the anterior surface of the eye is relatively routinely accomplished by topical means such as eye drops. However, the delivery of such therapeutic agents to the interior or back of the eye, even the inner portions of the cornea, presents unique challenges. In recent years drugs have become available that may be of use in treating diseases of the posterior segment of the eye, including pathologies of the posterior sclera, the uveal tract, the vitreous, the choroid, retina and optic nerve head (ONH). These new agents include anti-angiogenic agents, including protein kinase inhibitors, neuroprotectant agents such as brimonidine and memantine, and antiglaucoma agents such as prostaglandins, alpha- and beta-adrenergic agents (such as the alpha 2 adrenergic agonist brimonidine) and prostamides such as bimatoprost, as well as corticosteroids such as dexamethosone and triamcinolone.

However, a major limiting factor in the effective use of such agents is actually getting the agent to the affected tissue. The urgency to develop such methods can be inferred from the fact that the leading causes of vision impairment and blindness are posterior segment-linked diseases. These diseases include, without limitation, age-related macular degeneration (ARMD), proliferative vitreoretinopathy (PVR), diabetic macular edema (DME), and endophthalmitis. Glaucoma, which is often thought of as a condition of the anterior chamber affecting the flow (and thus the intraocular pressure (IOP)) of aqueous humor, also has a posterior segment component; indeed, certain forms of glaucoma are not characterized by high IOP, but mainly by retinal degeneration alone.

Generally, and depending in part on factors such as hydrophilicity, blood supply, specific activity, and nature of the drug, topical drug delivery can deliver therapeutic concentrations of the drug to anterior segment features such as the cornea, anterior chamber, iris, lens and cilary body of the eye, but drug delivery to posterior segment features such as the vitreous humor, retinal pigmented epithelium, retina and choroid is less effective. The usual route of drug administration for topical delivery is by systemic dosing or direct intraocular placement. Theoretically, drug applied topically to the eye can diffuse through the conjunctiva and sclera, and then penetrate the eye through the iris route or the retinal pigmented epithelium (RPE). This creates a very large diffusional path length and the tissues pose a considerable barrier, with the choroid blood-flow and the resistance of the conjunctiva and the RPE. In practice, topically applied ophthalmic drugs usually do not achieve therapeutic concentrations in the posterior segment tissues.

The corneal epithelium, retinal vessel endothelial cells and retinal pigmented epithelium (RPE) all comprise intercellular "tight junctions" preventing the free intercellular movement of small hydrophilic compounds. The RPE and the endothelial cells of the retinal vasculature comprises the "blood-retinal barrier", similar in some respects to the blood-brain barrier.

The retinal pigmented epithelium represents the outer blood-retinal barrier ("BRB"). The RPE is a "tight" ion transporting barrier and paracellular transport of solutes, especially of polar solutes, across the RPE from the choroid is restricted. The endothelium of the retinal blood vessels themselves comprises the inner blood-retinal barrier and offers considerable resistance to systemic penetration of drugs. Thus, for a drug to cross the BRB, it should either have a favorable membrane partition coefficient or be a substrate for one of the active membrane transporters present on the RPE or the endothelium of retinal blood vessels.

To this latter end, carrier-mediated membrane transport proteins at the plasma membrane surfaces allow the RPE to selectively transport nutrients, metabolites, and xenobiotics between the choriocapillaris (the network of small arteries underlying the retina) and cells of the distal retina. These specialized membrane transporters include amino acid, peptide, dicarboxylate, glucose, monocarboxylic acid, nucleoside, organic anion and organic cation transporters.

Mitra et al., U.S. Patent Publication No. 2005/0043246 have discussed using the peptide transport system for targeted delivery of tri- and di-peptide conjugates of acyclovir and ganciclovir to ocular tissue. This reference, and all other publications cited herein, is hereby incorporated by reference herein in its entirety.

Carrier-mediated membrane transport research in general is a rapidly developing and expanding area in the pharmaceutical sciences. It is increasingly clear that membrane transporters play a critical role in drug absorption and disposition. Membrane transporters play a pivotal role in delivering nutrients and aiding in the cellular detoxification process through their capacity to transport compounds in and out of the cells.

In a broad aspect, the present invention is directed to methods and compositions for utilizing membrane transporters to deliver ophthalmically effective bioactive agents, particularly those having a salutary effect upon diseases, disorders, and syndromes of the posterior segment of the eye, for the successful treatment of such disorders by designing membrane-targeted bioactive agents, or prodrugs of such bioactive agents, for the treatment of ocular diseases. By targeting membrane transporters, for example and without limitation, on the tight ocular epithelium such as cornea, conjunctiva and RPE, one may greatly increase absorption across these barriers and thus increase ocular bioavailability. In one embodiment, targeted transporters comprise the dicarboxylate, glucose, monocarboxylic acid, nucleoside, organic anion and organic cation transporters.

In another embodiment, the present invention is directed to novel compounds useful in the therapeutic treatment of an ocular condition, disease or disorder. Such compounds comprise an ophthalmically active agent joined to a membrane transporter carrier substrate. For example, in one aspect of this embodiment, an ophthalmically active compound is joined to a nucleoside for transmembrane transport via a nucleoside membrane transporter. In another aspect of this invention, an ophthalmically active compound is joined to an amino acid for transmembrane transport via an amino acid membrane transporter.

In certain aspects of the invention, the biologically active agent is joined to the carrier substrate with an ester or other hydrolysable linkage. In this way, the agent may be released at a location within a desired target cell or tissue, thus becoming activated at the precise site of action.

In another aspect, the present invention is drawn in part to the use of ocular membrane transport substrates as moieties for inclusion in the design of therapeutically active agents selectively targeted to locations within the posterior segment of the eye, such as, without limitation, the vitreous humor, the RPE, the retina, the choroid, the optic nerve and the sclera. Preferably, the targeted, transporter-containing membranes are conjunctival and RPE membranes.

In particular aspects of the invention the therapeutically active agents are preferably topically administered. This aspect of the invention also involves conjugates comprising "Trojan horses"; that is, a bioactive agent joined to a membrane transporter substrate, for the active transport of therapeutic agents across otherwise relatively impenetrable cell membranes and tissues.

However, in other aspects of the invention the therapeutically active agents are administered by other means, such other means including but not limited to intraocular or subconjunctival injection, implantation of an intraocular implant, or systemic administration.

In certain aspects the conjugates described in the present invention are designed as prodrugs. As used in the present application, a "prodrug" is a conjugate comprising a membrane transporter substrate joined to a bioactive agent with a tissue labile linkage, wherein the conjugate is therapeutically inactive or marginally active compared to the therapeutically active agent. The tissue labile linkage is preferably a hydrolysable linkage, most preferably an ester linkage, suitable for cleavage when situated within or close to the target tissue or site of action. Thus, these prodrugs are bioconverted back to the parent compound in the body.

In light of the present disclosure, the person of ordinary skill in the art is aware that efflux transporters also exist; these transporters decrease (rather than increase) the bioavailability of compounds across the conjunctiva or retina. This invention further teaches delivery of compounds with inhibitors of these transport mechanisms.

Biologically Active Agents

Bioactive agents useful in the present invention may include retinoids, prostaglandins, protein kinase inhibitors (such as tyrosine kinase inhibitors), α- or β-adrenoreceptor agonists or antagonists, dopaminergic agonists, cholinergic agonists, carbonic anhydrase inhibitors, guanylate cyclase activators, cannabinoids, endothelin, adenosine agonists, anti-angiogenic compounds, angiostatic compounds, and neuroprotectants.

More specifically, the bioactive agent may include non-steroidal anti-inflammatory drugs (NSAIDs), analgesics, or antipyretics; antihistamines, antibiotics, beta-blockers, steroids, such as corticosteroids, anti-neoplastic agents, immunosupressive agents, antiviral agents, and antioxidants.

Non-limiting examples of non-steroidal anti-inflammatories, analgesics, and antipyretics, include aspirin, acetaminophen, ibuprofen, naproxen, diclofenac, etodolac, fenoprofen, indomethacin, ketoprofen, oxaprozin, piroxicam, sulindac, diflunisal, mefenamic acid, and derivatives thereof.

As used herein, the term "derivative" refers to any substance that is sufficiently structurally similar to the material that it is identified as a derivative so as to have substantially similar functionality or activity, for example, therapeutic effectiveness, as the material when the substance is used in place of the material. The functionality of any derivative disclosed herein may be determined using conventional routine methods well known to persons of ordinary skill in the art.

Neuroprotective compounds include, without limitation, R,S-alpha-methyl-4-carboxyphenylglycine, (S)-2-amino-4-phosphonobutyrate, (2S,3S,4S)-alpha-carboxypropyl-glycine, (1S,3R)-1-aminocyclopentane-1,3-dicarboxyleic acid, nimodipine, nicardipine, ziconotide, dizocilpine, eliprodil, cerestat, D(−)-amino-5-phosphonopentanoic acid, selfotel, (+,−)-6-(1(2)H-tetrazol-5-yl)methyldecahydroisoquinoline-3-carboxylic acid, cis-(+,−)-4-[(2H-tetrazol-5-yl)methyl]piperidine-2-carboxylic acid, memantine, remacemide, dexanabinol, sinnabidiol, [2,3-dioxo-7-(1H-imidazol-1-yl)-6-nitro-1,2,3,4-tetrahydro-1-quinoxalinyl]acetic acid monohydrate, 7-chloro-3-methyl-3,4-dihydro-2H-1,2,4-benzothiadiazine S,S-dioxide, GV150525A, 1-aminocyclopropanecarboxylic acid, ACPCM, ACPCE, R(+)-3-amino-1-hydroxypyrrolid-2-one, R-cis-.beta.-methyl-3-amino-1-hydroxypyrrolid-2-one, ifenprodil, NPS-1506, 1,2-dihydrophthalazine, licositnel, clomthiazole, MDL-27192, ceresine, ascorbic acid, nitroarginine, lubeluzole, steroidal anti-inflammatories, non-steroidal antiinflammatories, alpha-phenyl-n-t-butyl-nitrone, AEOL 10150 or 10113 metalloporphirin, L,L isomer of Z-Leu-aminobutyric acid-CONH(CH$_2$)$_2$, AK295, Z-Leu-aminobutyric acid-CONH(CH$_2$)$_3$-morpholine, N-benzyloxycarbonyl-Val-Phe, z-VAD-CHO, z-DEVD, citicoline, TAK-147, etanercept, LY-287041, atropine and pralidoxime.

Examples of antihistamines include, and are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, exbrompheniramine, methdilazine, and trimprazine doxylamine, pheniramine, pyrilamine, chiorcyclizine, thonzylamine, and derivatives of each of these agents.

Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin, ofloxacin, gatofloxacin, moxifloxacin, clindamycin, metronidazole, gentamicin, lincomycin, tobramycin, vancomycin, polymyxin B sulfate, colistimethate, colistin, azithromycin, augmentin, sulfamethoxazole, trimethoprim, and derivatives thereof.

Examples of beta blockers (β-adrenergic receptor antagonists) include timolol, acebutolol, atenolol, labetalol, metoprolol, propranolol, and derivatives thereof.

Examples of corticosteroids include cortisone, prednisolone, triamcinolone, fluorometholone, dexamethasone, medrysone, loteprednol, fluazacort, hydrocortisone, prednisone triamcinolone, betamethasone, prednisone, methylprednisolone, triamcinolone acetonide, triamcinolone hexacatonide, paramethasone acetate, diflorasone, fluocinolone and fluocinonide, derivatives thereof, and mixtures thereof.

Examples of antineoplastic agents include adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppresive agents include cyclosporine, azathioprine, tacrolimus, and derivatives thereof.

Examples of antiviral agents include interferon gamma, zidovudine, amantadine hydrochloride, ribavirin, acyclovir, gancicylovir, valciclovir, dideoxycytidine, and derivatives thereof. In certain embodiments, preferred antiviral compounds do not include nacyclovir or gancicylovir.

Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamyl-cysteine, quercitin, lactoferrin, dihydrolipoic acid, citrate, *Ginkgo Biloba* extract, tea catechins, bilberry extract, vitamins E or esters of vitamin E, retinyl palmitate, and derivatives thereof.

Other bioactive agents—include squalamine, carbonic anhydrase inhibitors, protein kinase inhibitors, α1 and α2 adrenergic agonists, prostamides, prostaglandins, antiparasitics, antifungals, and derivatives thereof.

In a preferred embodiment of the invention, the biologically active agent or bioactive agent comprises a prostaglandin, a prostamide, a tyrosine kinase inhibitor, a glucocorticoid, an androgenic steroid, an estrogenic steroid, or a nonestrogenic steroid, an intracellular adhesion molecule inhibitor, or an alpha-2-adrenergic receptor agonist. In one specific embodiment, the bioactive agent is triamcinolone acetonide. In other embodiments, the bioactive agent comprises memantine, a tyrosine kinase inhibitor, or bimatoprost.

Prostaglandins affect retinal blood flow, and have roles in ocular inflammation, corneal neovascularization, and the disruption of the blood-retinal and blood-aqueous barriers; in another embodiment the therapeutic agent is a prostaglandin or a prostamide.

Protein kinases, particularly tyrosine kinases, are known to be involved in the progression of angiogenesis, particularly, though not exclusively, through the VEGF pathway. Tyrosine kinase inhibitors are thus valuable tools in the therapeutic treatment of aberrant angiogenesis, particularly ocular neovascularization.

It will be understood by the person of ordinary skill in the art that bioactive compounds other than the compounds or classes of compounds specifically recited herein may be useful in the methods of the present invention, and that such compounds may also be advantageously delivered to the posterior segment of the eye in accordance with the methods of the present invention.

Therapeutic Indications

The present invention is generally drawn to methods for treating the posterior segment of the eye. Preferably, the posterior segment of the eye comprises, without limitation, the uveal tract, vitreous, retina, choroid, optic nerve, and the retinal pigmented epithelium (RPE). The disease or condition related to this invention may comprise any disease or condition that can be prevented or treated by the action of the active drug upon a posterior part of the eye. While not intending to limit the scope of this invention in any way, some examples of diseases or conditions that can be prevented or treated by the action of an active drug upon the posterior part of the eye in accordance with the present invention include maculopathies/retinal degeneration such as macular edema, non-exudative age related macular degeneration (ARMD), exudative age related macular degeneration (ARMD), choroidal neovascularization, diabetic retinopathy, acute macular neuroretinopathy, central serous chorioretinopathy, cystoid macular edema, and diabetic macular edema; uveitis/retinitis/choroiditis such as acute multifocal placoid pigment epitheliopathy, Behcet's disease, birdshot retinochoroidopathy, infections (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vasuclar diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemiretinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigement epitheliitis. Preferably, the disease or condition is retinitis pigmentosa, proliferative vitreal retinopathy (PVR), age-related macular degeneration (ARMD), diabetic retinopathy, diabetic macular edema, retinal detachment, retinal tear, uveitis, or cytomegalovirus retinitis.

Topical Administration

Topical drug delivery to the anterior structures of the eye presents significant anatomic and physiologic hurdles. Low corneal permeability and rapid precorneal clearance of instilled drugs normally results in only a few percent of the applied dose being absorbed into the aqueous humor. Normal aqueous humor turnover continuously reduces the aqueous humor concentration of absorbed drug. Additionally the iridolenticular diaphragm prevents drug from reaching the posterior of the eye. Diffusion of drugs to the posterior chamber through the lens is not commonly thought to be feasible.

Therefore, the most likely route of posterior segment penetration for topically-administered ophthalmic drugs is through the conjunctiva and sclera. The three major tissue barriers for drug penetration through the conjunctival/scleral route for posterior drug delivery are the conjunctiva and sclera themselves, and the RPE-choroid.

The sclera has been shown to be permeable to solutes up to 70 kDa in molecular weight; however, once a compound has penetrated the conjunctiva and sclera it must further diffuse into the posterior chamber or enter the posterior segment through the RPE.

Unlike the sclera, the conjunctiva and RPE comprise tight epithelial barriers of multilayer and monolayer cells, respectively. The conjunctiva is lined by stratified columnar epithelium of two to seven cell layers resting on a continuous basal lamina and the RPE is made up of a tightly linked cuboidal monolayer epithelium that separates the outer surface of the neural retina from the choroid. Drug transport across these epithelial barriers can occur by passive (paracellular or transcellular) and active (transcellular involving carrier-mediated membrane transporter) means.

Diffusion of a compound to the sclera and subsequently into the retina is limited by the conjunctival and retinal pigmented epithelial barriers. However, if these barriers are overcome, then effective topical ophthalmic delivery to the posterior segment can be accomplished. By targeting e.g., conjunctival and RPE transporters one can circumvent the barriers to passive diffusion posed by these tissues.

The present application is directed in part to prodrugs and analogues of bioactive agents that target transporter systems such as these. A prodrug is an inactive or marginally active derivative of a known active drug, often possessing enhanced delivery characteristics. It is converted back to the parent compound by virtue of its enzymatic and/or chemical lability within the biologic system. The current invention applies to all compounds, including prodrugs, whose target tissue is comprised in the posterior of the eye that are targeted to membrane transporters. The functional groups of the parent compound amenable to prodrug derivatization can include carboxylic acids, hydroxyl groups, amine groups, sulfhydryl groups or any other functionality known to be amenable to prodrug derivatization. Prodrugs may comprise esters of hydroxyl containing groups contained in the bioactive agent. Other prodrugs of hydroxyl containing compounds include phosphate esters, hemiesters of dicarboxylic acids, acyloxyalkyl, Mannich bases and ethers.

The current invention also applies to derivatives of bioactive agents (including, without limitation, conjugates comprising a substrate and a bioactive agent) that posses their own intrinsic activity and are themselves substrates for e.g., conjunctival and RPE transporters. Unlike prodrugs, such analogues may not be inactive, and may not be converted back to the parent compound.

Direct Intraocular Administration

While topical administration is generally less traumatic than intraocular or subconjunctival administration of drugs to the eye, in some cases it will be necessary to directly (or more directly than topical administration permits) deliver the compositions of the present invention to the posterior segment of the eye.

The vitreous humor contained in the posterior chamber of the eye is quite viscous. Injection of a fluid or suspension of substantially lower viscosity into the posterior segment could therefore result in the presence of two somewhat immiscible phases or layers within the eye, which in turn can lead to the "pooling" of the injected fluid or suspension at the bottom of the posterior chamber and uneven or inconsistent dosing to tissues of the posterior segment.

To prevent this, the therapeutic agents, prodrugs and/or conjugates of the present invention may be suspended in a viscous formulation having a relatively high viscosity, such as one approximating that of the vitreous humor. Such viscous formulation comprises a viscosity-inducing component. The therapeutic agent of the present invention may be administered intravitreally as, without limitation, an aqueous injection, a suspension, an emusion, a solution, a gel or in a sustained release or extended release implant, either biodegradable or non-biodegradable.

The viscosity-inducing component preferably comprises a polymeric component and/or at least one viscoelastic agent, such as those materials that are useful in ophthalmic surgical procedures.

Examples of useful viscosity inducing components include, but are not limited to, hyaluronic acid, carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures thereof.

The molecular weight of the presently useful viscosity inducing components may be in a range up to about 2 million Daltons, such as of about 10,000 Daltons or less to about 2 million Daltons or more. In one particularly useful embodiment, the molecular weight of the viscosity-inducing component is in a range of about 100,000 Daltons or about 200,000 Daltons to about 1 million Daltons or about 1.5 million Daltons.

In one very useful embodiment, a viscosity inducing component is a polymeric hyaluronate component, for example, a metal hyaluronate component, preferably selected from alkali metal hyaluronates, alkaline earth metal hyaluronates and mixtures thereof, and still more preferably selected from sodium hyaluronates, and mixtures thereof. The molecular weight of such hyaluronate component preferably is in a range of about 50,000 Daltons or about 100,000 Daltons to about 1.3 million Daltons or about 2 million Daltons.

In one embodiment, the present compositions are comprised in, or comprise, a polymeric hyaluronate component in an amount in a range about 0.05% to about 0.5% (w/v). In a further useful embodiment, the hyaluronate component is present in an amount in a range of about 1% to about 4% (w/v) of the composition. In this latter case, the very high polymer viscosity forms a gel that slows the sedimentation rate of any suspended drug, and prevents pooling of injected drug product.

The therapeutic agent of this aspect of the claimed invention may include any or all salts, prodrugs, conjugates, or precursors of therapeutically useful agents, including those specifically identified herein.

In certain embodiments, the therapeutic component of the composition may comprise more than one therapeutic agent, so long as at least one such therapeutic agent is able to be transported across the plasma membrane, consistent with the transporter-targeting mechanisms described elsewhere in this specification. In other words, the therapeutic component of the composition may include a first therapeutic agent, and a second therapeutic agent, or a combination of therapeutic agents. Examples of therapeutic agents include those identified above in any combination. One or more of the therapeutic agents in such compositions may be formed as or present in particles or crystals.

The viscosity-inducing component is present in an effective amount in increasing, advantageously substantially increasing, and the viscosity of the composition. Without wishing to limit the invention to any particular theory of operation, it is believed that increasing the viscosity of the compositions to values well in excess of the viscosity of water, for example, at least about 100 cps at a shear rate of 0.1/second, compositions which are highly effective for placement, e.g., injection, into the posterior segment of an eye of a human or animal are obtained. Along with the advantageous placement or injectability of the present compositions into the posterior segment, the relatively high viscosity of the present compositions are believed to enhance the ability of the present compositions to maintain the therapeutic component (for example, comprising corticosteroid-containing particles) in substantially uniform suspension in the compositions for prolonged periods of time, for example, for at least about one week, without requiring resuspension processing. The relatively high viscosity of the present compositions may also have an additional benefit of at least assisting the compositions to have the ability to have an increased amount or concentration of the corticosteroid component, as discussed elsewhere herein, for example, while maintaining such corticosteroid component in substantially uniform suspension for prolonged periods of time.

Advantageously, the compositions of this aspect of the invention have viscosities of at least about 10 cps or at least about 100 cps or at least about 1000 cps, more preferably at least about 10,000 cps and still more preferably at least about 70,000 cps or more, for example up to about 200,000 cps or about 250,000 cps, or about 300,000 cps or more, at a shear rate of 0.1/second. In particular embodiments the present compositions not only have the relatively high viscosity noted above but also have the ability or are structured or made up so as to be effectively able to be placed, e.g., injected, into a posterior segment of an eye of a human or animal, preferably through a 27 gauge needle, or even through a 30 gauge needle.

The viscosity inducing components preferably are shear thinning components such that as the viscous formulation is passed through or injected into the posterior segment of an eye, for example, through a narrow aperture, such as 27 gauge needle, under high shear conditions the viscosity of the composition is substantially reduced during such passage. After such passage, the composition regains substantially its pre-injection viscosity so as to maintain the corticosteroid component particles in suspension in the eye.

Any ophthalmically acceptable viscosity-inducing component may be employed in accordance with the present invention. Many such viscosity-inducing components have been proposed and/or used in ophthalmic compositions used on or in the eye. The viscosity-inducing component is present in an amount effective in providing the desired viscosity to the composition. Advantageously, the viscosity-inducing component is present in an amount in a range of about 0.5% or about 1.0% to about 5% or about 10% or about 20% (w/v) of the composition. The specific amount of the viscosity inducing component employed depends upon a number of factors including, for example and without limitation, the specific viscosity inducing component being employed, the molecular weight of the viscosity inducing component being employed, the viscosity desired for the present composition being produced and/or used and similar factors.

In another embodiment of the invention, the transporter-targeted ophthalmically and biologically active drugs may be delivered intraocularly in a composition that comprises, consists essentially of, or consists of, a therapeutic agent comprising a bioactive agent and a transporter substrate, and a biocompatible polymer suitable for administration to the posterior segment of an eye. For example, the composition may, without limitation, comprise an intraocular implant. Some intraocular implants are described in publications including U.S. Pat. Nos. 6,726,918; 6,699,493; 6,369,116; 6,331,313; 5,869,079; 5,824,072; 5,766,242; 5,632,984; and 5,443,505, all of which are hereby incorporated by reference herein in their entirety.

The polymer in combination with the therapeutic agent may be understood to be a polymeric component. In some embodiments, the particles may comprise materials other than D,L-polylactide (PLA) or latex (carboxylate modified polystyrene beads). In certain embodiments, the polymer component may comprise a polysaccharide. For example, the polymer component may comprise a mucopolysaccharide. In at least one specific embodiment, the polymer component is hyaluronic acid.

However, in additional embodiments, the polymeric component may comprise any polymeric material useful in a body of a mammal, whether derived from a natural source or synthetic. Some additional examples of useful polymeric materials for the purposes of this invention include carbohydrate based polymers such as methylcellulose, carboxymethylcellulose, hydroxymethylcellulose hydroxypropylcellulose, hydroxyethylcellulose, ethyl cellulose, dextrin, cyclodextrins, alginate, hyaluronic acid and chitosan, protein based polymers such as gelatin, collagen and glycolproteins, and hydroxy acid polyesters such as bioerodable polylactide-coglycolide (PLGA), polylactic acid (PLA), polyglycolide, polyhydroxybutyric acid, polycaprolactone, polyvalerolactone, polyphosphazene, and polyorthoesters. Polymers can also be crosslinked, blended or used as copolymers in the invention. Other polymer carriers include albumin, polyanhydrides, polyethylene glycols, polyvinyl polyhydroxyalkyl methacrylates, pyrrolidone and polyvinyl alcohol.

Some examples of non-erodible polymers include silicone, polycarbonates, polyvinyl chlorides, polyamides, polysulfones, polyvinyl acetates, polyurethane, ethylvinyl acetate derivatives, acrylic resins, crosslinked polyvinyl alcohol and crosslinked polyvinylpyrrolidone, polystyrene and cellulose acetate derivatives.

These additional polymeric materials may be useful with any of the transporter-targeted therapeutic agents disclosed herein. For example, and without limitation, particles of PLA or PLGA may be coupled to a nucleoside-triamcinolone conjugate, the latter designed for targeting to the nucleoside transporter system. This insoluble tripartite conjugate will slowly erode over time, thereby continuously releasing the transporter-targeted triamcinolone conjugate. Once this conjugate reaches the RPE, retina, or other target tissue it is transported through the plasma membrane into the target tissue or cells where it is able to exert its activity.

Formulation Vehicles

Regardless of the mode of administration or form of therapeutic agent (e.g., in solution, suspension, as a topical, injectable or implantable agent), the transporter-targeted therapeutic compositions of the present invention will be administered in a pharmaceutically acceptable vehicle component. The therapeutic agent or agents may also be combined with a pharmaceutically acceptable vehicle component in the manufacture of a composition. In other words, a composition, as disclosed herein, may comprise a therapeutic component and an effective amount of a pharmaceutically acceptable vehicle component. In at least one embodiment, the vehicle component is aqueous-based. For example, the composition may comprise water.

In certain embodiments, the therapeutic agents are administered in a vehicle component, and may also include an effective amount of at least one of a viscosity inducing component, a resuspension component, a preservative component, a tonicity component and a buffer component. In some embodiments, the compositions disclosed herein include no added preservative component. In other embodiments, a composition may optionally include an added preservative component. In addition, the composition may be included with no resuspension component.

Formulations for topical or intraocular administration of the transporter-targeted ophthalmic agents (or implants or particles containing such agents) will preferably include a major amount of liquid water. The present compositions are preferably formulated in a sterile form, for example, prior to being used in the eye. The above-mentioned buffer component, if present in the intraocular formulations, is present in an amount effective to control the pH of the composition. The formulations may contain, either in addition to, or instead of the buffer component at least one tonicity component in an amount effective to control the tonicity or osmolality of the compositions. Indeed, the same component may serve as both a buffer component and a tonicity component. More preferably, the present compositions include both a buffer component and a tonicity component.

The buffer component and/or tonicity component, if either is present, may be chosen from those that are conventional and well known in the ophthalmic art. Examples of such buffer components include, but are not limited to, acetate buffers, citrate buffers, phosphate buffers, borate buffers and the like and mixtures thereof. Phosphate buffers are particularly useful. Useful tonicity components include, but are not limited to, salts, particularly sodium chloride, potassium chloride, any other suitable ophthalmically acceptably tonicity component and mixtures thereof. Non-ionic tonicity components may comprise polyols derived from sugars, such as xylitol, sorbitol, mannitol, glycerol and the like.

The amount of buffer component employed preferably is sufficient to maintain the pH of the composition in a range of about 6 to about 8, more preferably about 7 to about 7.5. The amount of tonicity component employed preferably is sufficient to provide an osmolality to the present compositions in a range of about 200 to about 400, more preferably about 250 to about 350, mOsmol/kg respectively. Advantageously, the present compositions are substantially isotonic.

The present compositions may include one or more other components in amounts effective to provide one or more useful properties and/or benefits to the present compositions. For example, although the present compositions may be substantially free of added preservative components, in other embodiments, the present compositions include effective amounts of preservative components, preferably such components that are more compatible with or friendly to the tissue in the posterior segment of the eye into which the composition is placed than benzyl alcohol. Examples of such preservative components include, without limitation, quaternary ammonium preservatives such as benzalkonium chloride ("BAC" or "BAK") and polyoxamer; biguanide preservatives such as polyhexamethylene biguandide (PHMB); methyl and ethyl parabens; hexetidine; chlorite components, such as stabilized chlorine dioxide, metal chlorites and the like; other ophthalmically acceptable preservatives and the like and mixtures thereof. The concentration of the preservative component, if any, in the present compositions is a concentration effective to preserve the composition, and (depending on the nature of the particular preservative used) is often and generally used in a range of about 0.00001% to about 0.05% (w/v) or about 0.1% (w/v) of the composition.

Active and Facilitated Transport

Specific carrier-mediated membrane transport proteins at the plasma membrane surfaces allow the RPE to selectively transport nutrients, metabolites, and xenobiotics between the choriocapillaris and cells of the distal retina. These specialized membrane transporters include amino acid, peptide, dicarboxylate, glucose, monocarboxylic acid, nucleoside, organic anion and organic cation transporters. Membrane transporters can play a critical role in drug absorption and disposition. Similarly, by targeting membrane transporters on the tight ocular epithelium such as cornea, conjunctiva and RPE, one may greatly increase absorption across these barriers and thus increase ocular bioavailability.

Molecular and functional evidence of membrane transporters in the conjunctiva and retina/RPE across different species has been reported. These transporters can offer site-specific targeting for enhanced drug delivery to the posterior ocular tissues. These membrane transporters include amino acid, peptide, glucose, monocarboxylic acid, nucleoside and organic cation transporters. Membrane barriers such as the efflux pumps including multidrug resistance protein (P-gp) and multidrug resistance-associated protein (MRP) pumps will also impact availability.

TABLE 1

| Transporter | Species | Tissue | References |
|---|---|---|---|
| Aquaporins | Human, rat | Retina | 41, 42 |
| Amino Acid Transporters | Mouse | Retina | 43 |
|  | Rabbit | conjunctiva | 44, 45 |
|  | Rat | BRB | 46 |
| Dicarboxylate Transporters | Mouse | Retina, RPE | 47 |
| Peptide Transporter (PepT) | Rabbit | Conj., RPE | 48, 49 |
|  | Bovine, human, rat | retina | 50, 51 |
| Folate Transporter | Human, rat | RPE | 52 |
| GABA Transporter (GAT) | Bullfrog | Retina, RPE | 53, 54 |
|  | Mouse, Rabbit, Rat | Retina | 55, 56, 57, 58 |
| Glucose Transporters | Bovine | Retina, RPE | 59, 60 |
|  | Human | Conj., retina, RPE | 61, 62, 63 |
|  | Rabbit | Conj. | 64, 65, 34, 66 |
|  | Rat | Retina, RPE |  |
| Glutamate Transporters | Rat, bullfrog | Retina | 70-71 |
| GLAST/GLT/EAAC/EAAT | Human, bovine | Retina | 72-74 |
| Monocarboxylic acid (MCT) | Rabbit | Conj. | 75 |
|  | Human | Retina, RPE | 76, 77 |
|  | Bovine, porcine | RPE | 78, 79 |
|  | Rat | Retina, RPE, inner BRB | 80-84 |
| MRP Efflux Transporter | Human, porcine | RPE | 85, 86 |

TABLE 1-continued

| Transporter | Species | Tissue | References |
|---|---|---|---|
| Nucleoside Transporter | Rabbit | Conj., retina | 87-89 |
| | Human | Retina, RPE | 89, 90 |
| Organic anion transporters | | | |
| Oatp-2 | Rat | Retina, RPE | 91, 92 |
| Oatp-3 | Mouse | Retina, RPE | 92, 93 |
| | Rat | | |
| Oatp-E | Rat | Retina, RPE | 94 |
| Organic Cation transporters | | | |
| Non-OCT-type | Human | RPE | 95 |
| OCT-type | Mouse | Retina, RPE | 96 |
| OCT-type | Rabbit | Conj. | 134 |
| P-glycoprotein Efflux | Human | RPE | 97, 98 |
| | Rabbit | Conj. | 99 |
| | Rat | Retinal endothelium | 100 |

The reference numbers correspond to the following publications, which are incorporated by reference herein in their entirety.

34. Horibe Y, Hosoya K, Kim K J, Ogiso T, Lee V H. *Polar solute transport across the pigmented rabbit conjunctiva: Size dependence and the influence of 8-bromo cyclic adenosine monophosphate. Pharm Res.* 14(9) (1997) 1246-1251.
41. Patil R V, Saito I, Yang X, Wax M B. *Expression of aquaporins in the rat ocular tissue. Exp Eye Res.* 64 (1997) 203-209.
42. Tenckhoff S, Hollborn M, Kohen L, Wolf S, Wiedemann P, Bringmann A. *Diversity of aquaporin mRNA expressed by rat and human retinas. Neuroreport.* 16(1) (2005) 53-6.
43. Gu S, Roderick H L, Camacho P, Jiang J X., *Characterization of an N-system amino acid transporter expressed in retina and its involvement in glutamine transport., J Biol. Chem.* 276(26) 2001 Jun. 29 24137-44.
44. Kompella U B, Kim K J, Shiue M H, Lee V H., *Possible existence of Na(+)-coupled amino acid transport in the pigmented rabbit conjunctiva.* 57(15) *Life Sci.* 1995 1427-31.
45. Hosoya K, Horibe Y, Kim K J, Lee V H., *Na(+)-dependent L-arginine transport in the pigmented rabbit conjunctiva. Exp Eye Res.* 65(4) 1997 October 547-53.
46. Tornquist P, Alm A., *Carrier-mediated transport of amino acids through the blood-retinal and the blood-brain barriers. Graefes Arch Clin Exp Opthalmol.* 224(1) 1986 21-5.
47. George R L, Huang W, Naggar H A, Smith S B, Ganaphthy V. *Transport of N-acetylaspartate via murine sodium/dicarboxylate cotransporter NaDC3 and expression of this transporter and aspartoacylase II in ocular tissues in mouse. Biochim Biophys Acta.* 1690(1) (2004) 63-9.
48. Basu S K, Haworth I S, Bolger M B, Lee V H L. *Proton-driven dipeptide uptake in primary cultured rabbit conjunctival epithelial cells. Invest Opthalmol V is Sci.* 39 (1998) 2365-2373.
49. Atluri H, Anand B S, Patel J, Mitra A K., *Mechanism of a model dipeptide transport across blood-ocular barriers following systemic administration. Exp Eye Res.* 78(4) 2004 April 815-22.
50. Ocheltree S M, Keep R F, Shen H, Yang D, Hughes B A, Smith D E. *Preliminary investigation into the expression of proton-coupled oligopeptide transporters in neural retina and retinal pigment epithelium (RPE): lack of functional activity in RPE plasma membranes. Pharm Res.* 20(9) (2003) 1364-72.
51. Berger U V, Hediger M A., *Distribution of peptide transporter PEPT2 mRNA in the rat nervous system. Anat Embryol (Berl).* 199(5) 1999 May 439-49.
52. Chancy C D, Kekuda R, Huang W, Prasad P D, Kuhnel J M, Sirotnak F M, Roon P, Ganaphthy V, Smith S B. *Expression and differential polarization of the reduced-folate transporter-1 and the folate receptor α in mammalian retinal pigment epithelium. J Biol. Chem.* 275(27) (2000) 20676-20684.
53. Peterson W M, Miller S S. *Identification and functional characterization of a dual GABA/taurine transporter in the bullfrog retinal pigment epithelium. J Gen Physiol.* 106(6) (1995) 1089-122.
54. Zhao J W, Du J L, Li J S, Yang X L. *Expression of GABA transporters on bullfrog retinal Muller cells. Glia.* 31(2) (2000) 104-17.
55. Ruiz M, Egal H, Sarthy V, Qian X, Sarkar H K. *Cloning, expression, and localization of a mouse retinal gamma-aminobutyric acid transporter. Invest Opthalmol V is Sci.* 35(12) (1994) 4039-48.
56. Hu M, Bruun A, Ehinger B. *Expression of GABA transporter subtypes (GAT1, GAT3) in the adult rabbit retina. Acta Opthalmol Scand.* 77(3) (1999) 255-60.
57. Brecha N C, Weigmann C. *Expression of GAT-1, a high-affinity gamma-aminobutyric acid plasma membrane transporter in the rat retina. J Comp Neurol.* 345(4) (1994) 602-11.
58. Honda S, Yamamoto M, Saito N. *Immunocytochemical localization of three subtypes of GABA transporter in rat retina. Brain Res Mol Brain Res.* 33(2) (1995) 319-25.
59. Knott R M, Robertson M, Forrester J V. *Regulation of glucose transporter (GLUT3) and aldose reductase mRNA in bovine retinal endothelial cells and retinal pericytes in high glucose and high galactose culture. Diabetologia.* 36(9) (1993) 808-12.
60. To C H, Cheung K K, Chiu S H, Lai H M, Lung K S. *The saturation characteristics of glucose transport in bovine retinal pigment epithelium. Yan Ke Xue Bao.* 14(3) (1998) 126-9.
61. Harik S I, Kalaria R N, Whitney P M, Anderson L, Lundahl P, Ledbetter S R, Perry G. *Glucose transporters are abundant in cells with "occluding" junctions at the blood-eye barriers. Proc Natl Acad Sci USA.* 87(11) (1990) 4261-4.
62. Gherzi R, Melioli G, De Luca M, D'Agostino A, Guastella M, Traverso C E, D'Anna F, Franzi A T, Cancedda R. *High expression levels of the "erythroid/brain" type glucose transporter (GLUT1) in the basal cells of human eye conjunctiva and oral mucosa reconstituted in culture. Exp Cell Res.* 195(1) (1991) 230-6.
63. Mantych G J, Hageman G S, Devaskar S U. *Characterization of glucose transporter isoforms in the adult and developing human eye. Endocrinology.* 133(2) (1993) 600-7.
64. Shi X P, Candia O A. *Active sodium and chloride transport across the isolated rabbit conjunctiva. Curr Eye Res.* 14(10) (1995) 927-35.
65. Hosoya K, Kompella U B, Kim K J, Lee V H. *Contribution of Na(+)-glucose cotransport to the short-circuit current in the pigmented rabbit conjunctiva. Curr Eye Res.* 15(4) (1996) 447-51.
66. Horibe Y, Hosoya K, Kim K J, Lee V H. *Kinetic evidence for Na(+)-glucose co-transport in the pigmented rabbit conjunctiva. Curr Eye Res.* 16(10) (1997) 1050-5.
67. Tsukamoto H, Mishima H K, Kurokawa T, Kiuchi Y, Sato E, Ishibashi S. *Isoforms of glucose transporter in the iris-ciliary body. Jpn J Opthalmol.* 39(3) (1995) 242-7.

68. Watanabe T, Mio Y, Hoshino F B, Nagamatsu S, Kirosawa K, Nakahara K. *GLUT2 expression in the rat retina: location at the apical ends of Muller cells*. Brain Res. 655(1-2) (1994) 128-34.

69. Harik S I, Kalaria R N, Whitney P M, Anderson L, Lundahl P, Ledbetter S R, Perry G. *Glucose transporters are abundant in cells with "occluding" junctions at the blood-eye barriers*. Proc Natl Acad Sci USA. 87(11) (1990) 4261-4.

70. Schultz

71. Zhao J W, Yang X L., *Glutamate transporter EAAC1 is expressed on Muller cells of lower vertebrate retinas*. J Neurosci Res. 66(1) 2001 Oct. 1 89-95.

72. Inoue K, Sakaitani M, Shimada S, Tohyama M., *Cloning and expression of a bovine glutamate transporter*. Brain Res Mol Brain Res. 28(2) 1995 February 343-8.

73. Rauen T., *Diversity of glutamate transporter expression and function in the mammalian retina*. Amino Acids. 19(1) 2000 53-62

74. Pignataro L, Sitaramayya A, Finnemann S C, Sarthy V P. *Nonsynaptic localization of the excitatory amino acid transporter 4 in photoreceptors*. Mol Cell Neurosci. 28(3) (2005) 440-51.

75. Horibe Y, Hosoya K, Kim K J, Lee V H. *Carrier-mediated transport of monocarboxylate drugs in the pigmented rabbit conjunctiva*. Invest Opthalmol V is Sci. 39(8) (1998) 1436-43.

76. Knott R M, Robertson M, Muckersie E, Folefac V A, Fairhurst F E, Wileman S M, Forrester J V. *A model system for the study of human retinal angiogenesis: activation of monocytes and endothelial cells and the association with the expression of the monocarboxylate transporter type 1 (MCT-1)*. Diabetologia. 42(7) (1999) 870-7.

77. Philp N J, Wang D, Yoon H, Hjelmeland L M. *Polarized expression of monocarboxylate transporters in human retinal pigment epithelium and ARPE-19 cells*. Invest Opthalmol V is Sci. 44(4) (2003) 1716-21.

78. Kenyon I, Yu K, La Cour M, Miller S S. *Lactate transport mechanisms at apical and basolateral membranes of bovine retinal pigment epithelium*. Am J. Physiol. 267 (1994) C1561-C1573.

79. Hamann S, Kiilgaard J F, Ia Cour M, Prause J U, Zeuthen T. *Cotransport of H+, lactate, and H2O in porcine retinal pigment epithelial cells*. Exp Eye Res. 76(4) (2003) 493-504.

80. Alm A, Tornquist P. *Lactate transport through the blood-retinal and the blood-brain barrier in rats*. Ophthalmic Res. 17 (1985) 181-184.

81. Philp N J, Yoon H, Grollman E F. *Monocarboxylate transporter MCT1 is located in the apical membrane and MCT3 in the basal membrane of rat RPE*. Am J Physiol. 274(6 Pt 2) (1998) R1824-8.

82. Gerhart D Z, Leino R L, Drewes L R. *Distribution of monocarboxylate transporters MCT1 and MCT2 in rat retina*. Neuroscience. 92(1) (1999) 367-75.

83. Bergersen L, Johannsson E, Veruki M L, Nagelhus E A, Halestrap A, Sejersted O M, Ottersen O P. *Cellular and subcellular expression of monocarboxylate transporters in the pigment epithelium and retina of the rat*. Neuroscience. 90(1) (1999) 319-31.

84. Hosoya K, Kondo T, Tomi M, Takanaga H, Ohtsuki S, Terasaki T. *MCT1-mediated transport of L-lactic acid at the inner blood-retinal barrier: a possible route for delivery of monocarboxylic acid drugs to the retina*. Pharm Res. 18(12) (2001) 1669-76.

85. Aukunuru J V, Sunkara G, Bandi N, Thoreson W B, Kompella U B. *Expression of multidrug resistance-associated protein (MRP) in human retinal pigment epithelial cells and its interaction with BAPSG, a novel aldose reductase inhibitor*. Pharm Res. 18(5) (2001) 565-72.

86. Steuer H, Jaworski A, Elger B, Kaussmann M, Keldenich J, Schneider H, Stoll D, Schlosshauer B. *Functional characterization and comparison of the outer blood-retina barrier and the blood-brain barrier*. Invest Opthalmol V is Sci. 46(3) (2005) 1047-1053.

87. Blazynski C. *The accumulation of [3H]phenylisopropyl adenosine ([3H]PIA) and [3H]adenosine into rabbit retinal neurons is inhibited by nitrobenzylthioinosine (NBI)*. Neurosci Lett. 121(1-2) (1991) 1-4.

88. Hosoya K, Horibe Y, Kim K J, Lee V H. *Nucleoside transport mechanisms in the pigmented rabbit conjunctiva*. Invest Opthalmol V is Sci. 39(2) (1998) 372-7.

89. Majumdar S, Macha S, Pal D, Mitra A K. *Mechanism of ganciclovir uptake by rabbit retina and human retinal pigmented epithelium cell line ARPE-19*. Curr Eye Res. 29(2-3) (2004) 127-36.

90. Williams E F, Ezeonu I, Dutt K. *Nucleoside transport sites in a cultured human retinal cell line established by SV-40 T antigen gene*. Curr Eye Res. 13(2) (1994) 109-18.

91. Gao B, Wenzel A, Grimm C, Vavricka S R, Benke D, Meier P J, Reme C E. *Localization of organic anion transport protein 2 in the apical region of rat retinal pigment epithelium*. Invest Opthalmol V is Sci. 43(2) (2002) 510-4.

92. Ito A, Yamaguchi K, Onogawa T, Unno M, Suzuki T, Nishio T, Suzuki T, Sasano H, Abe T, Tamai M. *Distribution of organic anion-transporting polypeptide 2 (oatp2) and oatp3 in the rat retina*. Invest Opthalmol V is Sci. 43(3) (2002) 858-63.

93. Walters H C, Craddock A L, Fusegawa H, Willingham M C, Dawson P A., *Expression, transport properties, and chromosomal location of organic anion transporter subtype 3*. Am J Physiol Gastrointest Liver Physiol. 279(6) 2000 December G1188-200.

94. Ito A, Yamaguchi K, Tomita H, Suzuki T, Onogawa T, Sato T, Mizutamari H, Mikkaichi T, Nishio T, Suzuki T, Unno M, Sasano H, Abe T, Tamai M. *Distribution of rat organic anion transporting polypeptide-E (oatp-E) in the rat eye*. Invest Opthalmol V is Sci. 44(11) (2003) 4877-4884.

95. Han Y H, Sweet D H, Hu D N, Pritchard J B. *Characterization of a novel cationic drug transporter in human retinal pigment epithelial cells*. J Pharmacol Exp Ther. 296(2) (2001) 450-7.

96. Rajan P D, Kekuda R, Chancy C D, Huang W, Ganaphthy V, Smith S B. *Expression of the extraneuronal monoamine transporter in RPE and neural retina*. Curr Eye Res. 20(3) (2000) 195-204.

97. Kennedy B G, Mangini N J. *P-glycoprotein expression in human retinal pigment epithelium*. Mol Vis. 11(8) (2002) 422-30.

98. Steuer H, Jaworski A, Elger B, Kaussmann M, Keldenich J, Schneider H, Stoll D, Schlosshauer B. *Functional characterization and comparison of the outer blood-retina barrier and the blood-brain barrier*. Invest Opthalmol V is Sci. 46(3) (2005) 1047-1053.

99. Saha P, Yang J J, Lee V H. *Existence of a p-glycoprotein drug efflux pump in cultured rabbit conjunctival epithelial cells*. Invest Opthalmol V is Sci. 39(7) (1998) 1221-6.

100. Greenwood J. *Characterization of a rat retinal endothelial cell culture and the expression of P-glycoprotein in* brain and retinal endothelium in vitro. *J Neuroimmunol.* 39(1-2) (1992) 123-32.

134. Ueda H, Horibe Y, Kim K J, Lee V H., *Functional characterization of organic cation drug transport in the pigmented rabbit conjunctiva. Invest Opthalmol V is Sci.* 41 (3) (2000) 870-6.

Conditions affecting the posterior segment of the eye that may be more effectively treated using the transporter-targeted methods and composition of the present invention include those benefiting from reduction or control of retinal pigment epithelium (RPE) and/or glial migration, and the diseases or conditions related thereto. Thus, certain of the compositions disclosed herein can be used to treat a disease or condition wherein migration or proliferation of retinal pigment epithelium or glial cells causes or contributes to the cause of said disease or condition. The relationship may be direct or indirect, and the migration or proliferation retinal pigment epithelium or glial cells may be a root cause of said disease or condition, or may be a symptom of another underlying disease or condition. While not intending to limit the scope of the invention in any way, the following are examples of the types of diseases or conditions treated by the disclosed method: non-exudative age related macular degeneration, exudative age related macular degeneration, choroidal neovascularization, acute macular neuroretinopathy, cystoid macular edema, diabetic macular edema, Behcet's disease, diabetic retinopathy, retinal arterial occlusive disease, central retinal vein occlusion, uveitic retinal disease, retinal detachment, trauma, conditions caused by laser treatment, conditions caused by photodynamic therapy, photocoagulation, radiation retinopathy, epiretinal membranes, proliferative diabetic retinopathy, branch retinal vein occlusion, anterior ischemic optic neuropathy, non-retinopathy diabetic retinal dysfunction, and retinitis pigmentosa.

EXAMPLES

Example 1

Amino Acid Transporters

A $Na_1$-coupled L-arginine transport system has been characterized in the rabbit conjunctiva. The transport system of this transport system displays directionality (mucosal-to-serosal), and is inhibited by excess L-Arg, basic amino acids, large neutral amino acids, and nitric oxide synthase (NOS) inhibitors. The amino acid transport system $B^{0,+}$ is also present in the conjunctival transport of NOS inhibitors. Other amino acid transporters such as GABA, glutamate, glycine, taurine, tryptophan and proline have been characterized on the surface of cells of the retina/RPE.

Armed with this knowledge, amino acid prodrugs of, as non-limiting examples, the FDA-approved ophthalmic drug bimatoprost, and the tyrosine kinase inhibitor Compound 1 can be synthesized.

a) The person or ordinary skill in the art using convention methodology and materials can synthesize the glycyl ester of the tyrosine kinase inhibitor Compound 1. Methods for the construction of this and similar tyrosine kinase inhibitors can be found in U.S. patent application Ser. No. 11/180,496, hereby incorporated by reference herein in its entirety. The structure of the prodrug is as follows:

Glycyl Ester of Compound 1

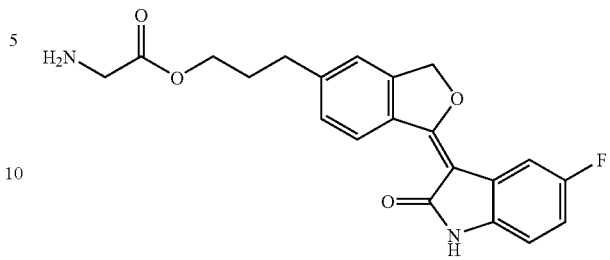

b) Similarly the person or ordinary skill in the art using convention methodology and materials can also synthesize a glycyl ester of the prostamide brimatoprost. The structure of this prodrug is as follows:

Glycyl Ester of Bimatoprost

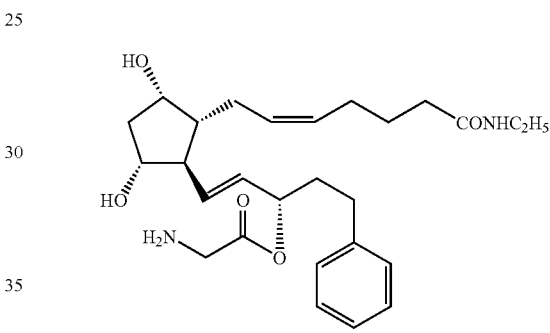

c) The person or ordinary skill in the art using convention methodology and materials can synthesize the tryptophyl ester of the tyrosine kinase inhibitor Compound 1. The structure of the prodrug is as follows:

Tryptophyl Ester of Compound 1

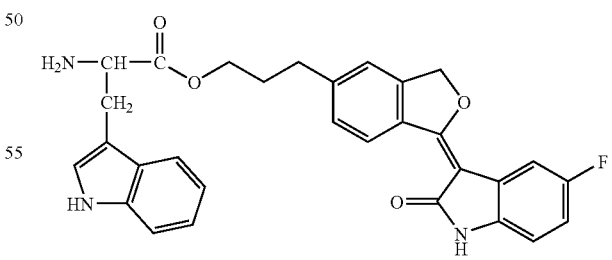

d) The person or ordinary skill in the art using convention methodology and materials can synthesize the tryptophyl ester of the tyrosine kinase inhibitor Compound 1. The structure of the prodrug is as follows:

Tryptophyl Ester of Bimatoprost

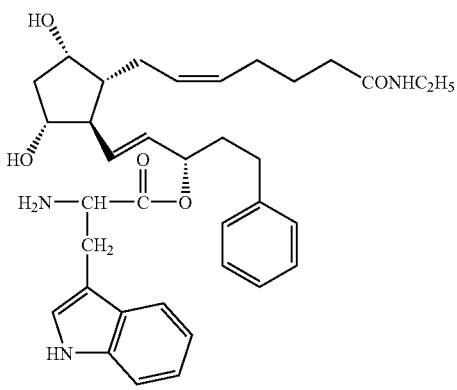

It will be understood that these prodrug compounds are designed to be able to be transported across the cell membrane using one or more amino acid transporter, and to be hydrolyzed by esterases contained in the cell to unmask the therapeutic moieties at or near their site of action.

Example 2

Peptide Transporters

Peptide transporters have significant pharmacological and pharmacokinetic relevance to the transport of various peptide-like or peptidomimetic drugs such as β-lactam antibiotics, anti-cancer agents, renin inhibitors, and several angiotensin-converting enzyme inhibitors across various epithelia. A model dipeptide glycylsarcosine has been shown to exist in the RPE. A proton-driven carrier-mediated dipeptide transporter has been functionally identified in primary cultured rabbit conjunctival epithelium.

As a non-limiting example, without any limitation, the glycylsarcosine esters of bimatoprost and the tyrosine kinase inhibitor Compound 1 can be synthesized by one of ordinary skill in the art using conventional organic chemistry synthesis techniques.

a) Glycylsarcosine Ester of Compound 1

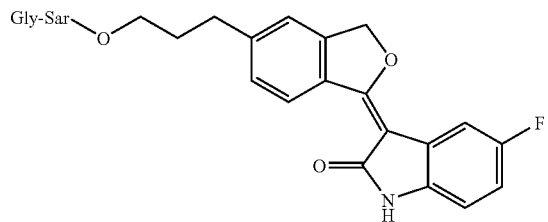

b) Glycylsarcosine Ester of Bimatoprost

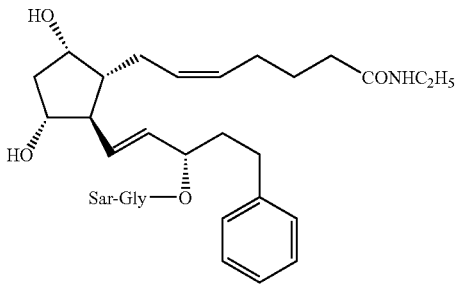

Example 3

Monocarboxylic Acid Transporters

Monocarboxylates such as acetate, propionate, lactate, pyruvate and ketone bodies are transported by $H^+$-coupled, $Na^+$-coupled or anion-exchange carrier-mediated monocarboxylic acid transporters. The presence of a $Na^+$ dependent monocarboxylate transporter in the pigmented rabbit conjunctiva has been shown. The transporter displays directionality in favor of the tear-to-scleral direction.

Monocarboxylic acids are transported in the direction of the sclera across the tears. However, in the RPE, the monocarboxylic acids are transported in the direction of the choroid from the RPE. Therefore it is important that the prodrug undergo facile hydrolysis upon penetration of the conjunctiva. As with the other examples disclosed herein, esters are good prodrug choices for this purpose.

As a non-limiting example, without any limitation, the succcinate esters of bimatoprost and the tyrosine kinase inhibitor Compound 1 can be synthesized by one of ordinary skill in the art using conventional organic chemistry synthesis techniques.

a) Succinate Ester of Compound 1

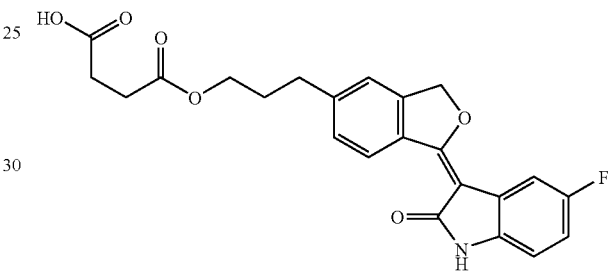

b) Succinate Ester of Bimatoprost

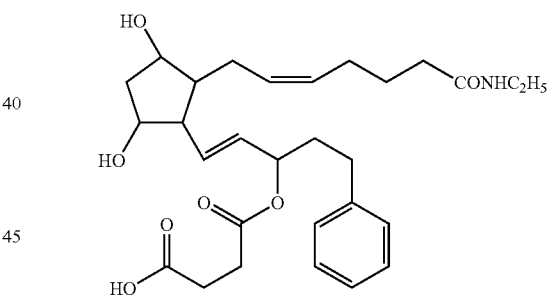

Example 4

Organic Acid Transporters

Further embodiments of the present invention comprise drugs that are substrates for organic acid transporters that can be co-administered into the vitreous with probenecid to prolong the vitreal half-life. In this embodiment, as well as in other embodiments, drugs can also be formulated with probenecid or other inhibitors of organic acid transporters in the form of implants and microspheres.

Example 5

Nucleoside Transporters

Nucleoside transporters exist in rabbit pigmented conjunctiva epithelium and mediate transporter of nucleoside-linked molecules in the tear-to-sclera direction. Na⁺-dependent and Na⁺-independent nucleoside transport processes appeared to be localized on the tear side of the rabbit conjunctiva. Nucleoside transporters were also identified in rabbit retina and human RPE cell lines. This transporter involvement can allow 10 to 100 times more drug to be absorbed than by paracellular diffusion. This was shown to be the case with cidofovir, an acyclic cytosine nucleoside analog.

a) As a non-limiting example, the uridine prodrug of bimatorpost and the tyrosine kinase inhibitor Compound 1 can be synthesized:

Uridine Diester of Compound 1

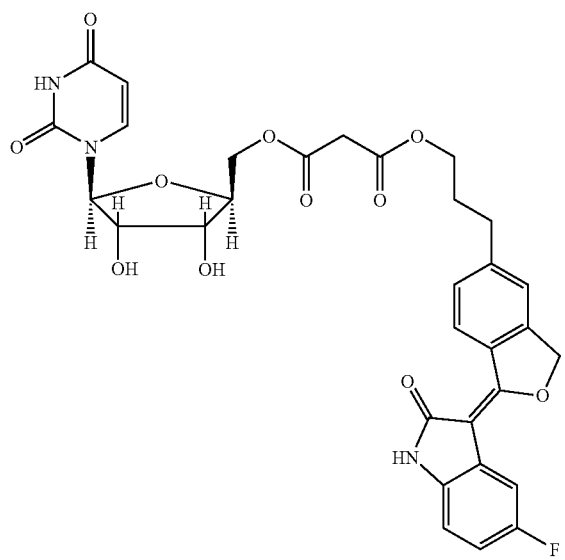

b) Uridine Diester of Bimatoprost

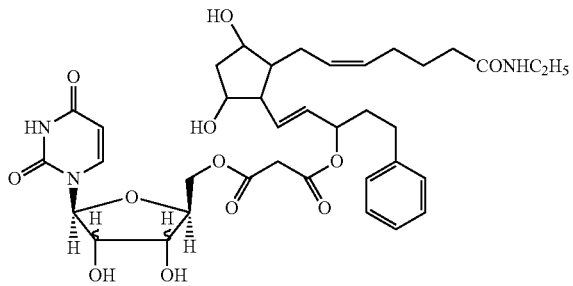

Example 6

Organic Cation Transporters

Transport of organic cations is mediated by substrate-specific, sodium-dependent transporters and by less specific sodium-independent transporters. Two major families of organic cation transporters have been identified: organic cation transporters (OCT) and organic cation/carnitine transporters (OCTN). The permeability of the pigmented rabbit conjunctiva to guanidine, a substrate commonly used to characterize organic cationic transporters (OCT), has been assessed. It was shown that the permeability of guanidine was 5.4 times greater in the mucosal to serosal direction as opposed to the serosal to mucosal.

A facilitative carrier-mediated system in the conjunctival epithelial cells is postulated as a carrier similar to OCT1, OCT2 and OCT3. Organic cations are transported in the direction of the sclera across the tears. However, in the RPE the organic cations are transported in the direction of the choroid from the RPE. Therefore in this tissue it may be important that a prodrug undergo facile hydrolysis upon penetration of the conjunctiva. Esters are good prodrugs for this purpose.

The following, non-limiting examples can be synthesized by the ordinarily skilled chemist using conventional chemical techniques:

a) Lysyl Ester of Compound 1

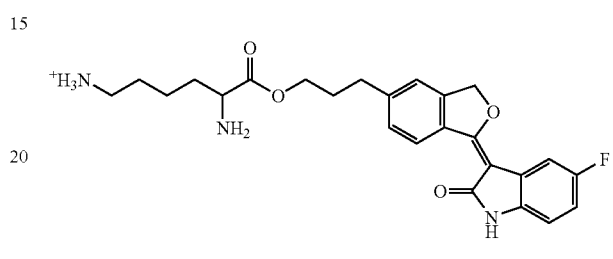

b) Lysyl Ester of Bimatoprost

The lysine ester of bimatorprost is synthesized by suspending bimatoprost in a 1:1 solution of N,N-dimethyl formamide (DMF): pyridine and a 5-fold excess of the Lysine Chloride at room temperature. The reaction is allowed to proceed for 2-3 days at room temperature until completion, as ascertained by thin layer chromatographic (TLC) analysis. The pyridine and DMF is removed in vacuo and the product precipitated from the acid chloride. The precipitate is purified by silica gel chromatography and recrystallized from a benzene-methanol mixture to yield the purified product.

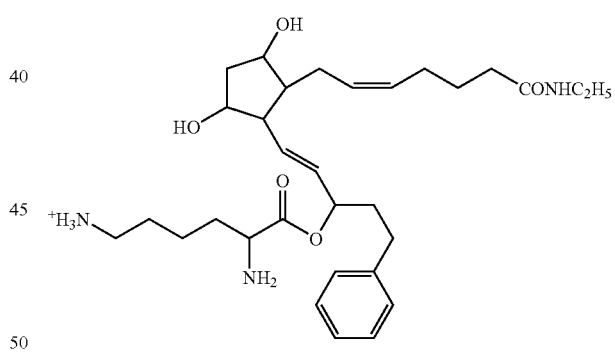

Example 7

Use of Topical Formulation of Compound 1 for the Treatment of Macular Degeneration A 65-year-old male presents with advanced (wet) age-related macular degeneration in the left eye. Dilated examination of the retina reveals nascent angiogenesis and edema, characterized by the presence of both fine blood vessels and retinal edema underlying the macula.

The patient is given a regimen comprising three times daily administration of a topical formulation of the lysine ester of the tyrosine kinase inhibitor Compound 1 illustrated in Example 6, above. The formulation is made slightly hypotonic with reference to the tonicity of the aqueous humor, and is buffered at a pH 7.2. The formulation is made so as to deliver between about 0.5 µg of the lysyl ester/TKI prodrug to the patent's left eye per day.

After two months of treatment the patient's left eye is given a dilated retinal examination. Edema has decreased to between about one third to about one fourth of its original size. Neither angiogenic infiltration of the macula nor the degeneration of visual acuity has progressed noticeably since the initiation of treatment.

Another full retinal examination given at six months after the onset of treatment reveals that visual acuity has increased significantly, that macular edema has now disappeared, and the fine blood vessels formerly underlying the macula have retreated, leaving morphologically and functionally normal appearing retinal tissue. The patient reports notably less blurry and distorted vision.

Example 8

A 73-year-old female complains of blurred central vision. Dilated examination of her eyes reveals the presence of cystic macular edema in her right eye.

The patient is given an intraocular injection of an antiinflammatory agent designed to utilize a membrane bound glucose transporter in the posterior segment. This compound is a D-glucopyranosyl ester of dexamethasone, having a structure as follows.

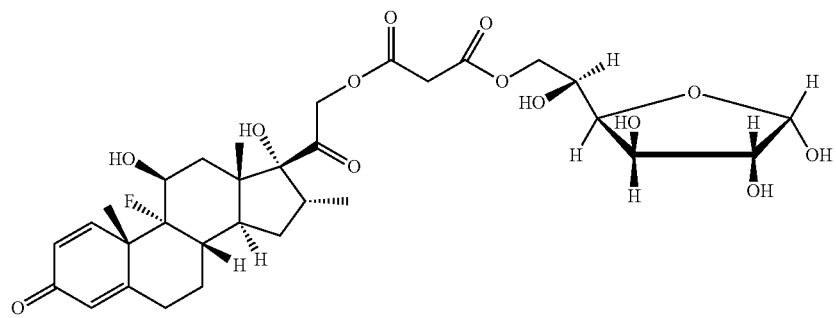

This prodrug is contained in a bioerodable monolithic polylactic acid-polyglycolic acid copolymer (PLGA) implant, as described in U.S. Pat. No. 6,726,918, hereby incorporated by reference herein in its entirety. The implant is injected in small volume (about 200 µl) of a solution of 1.0 (w/v) % hyaluronic acid, having a pH of between about 7.2 and an osmolality of about 400 mOSM/kg, and is designed to deliver about 0.05 µg of the prodrug to retinal tissues within 48 hours, and to continually release about 0.03 µg/ml of the prodrug to the posterior segment over a period of at least three weeks.

The patient is given a topical dose of 0.15% (w/v) brimonidine tartrate in the right eye twice daily following the implantation, and the intraocular pressure is monitored for the subsequent two weeks.

After one month, the patient's right eye is examination after dilation. Evidence of the cystic macular edema has disappeared from the patient's retina, and clarity of focus has returned to the patient's vision.

Example 9

A 36-year-old patient having been diagnosed with sickle cell disease 10 years previously presents with blurred vision in both eyes. Retinal examination under dilation reveals regions of macular ischemia and subsequent retinal neovascularization in the form of neovascular fronds or "sea fans" in both eyes. Additionally, small regions of macular edema are visible.

The patient is treated with intravitreal injection of 0.1% (w/v) of the succinyl ester of bimatoprost.

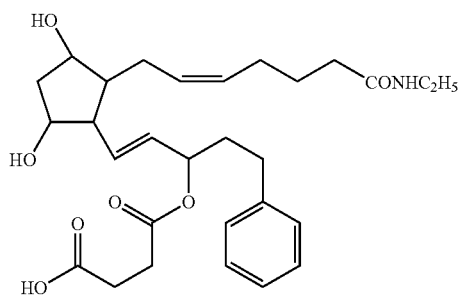

The prodrug is delivered in a solution of 200 µl of 1% (w/v) hyaluronic acid at pH 7.2.

One month following the intravitreal injection, the patient is again given a retinal examination under dilation. The regions of retinal neovascularization and edema have diminished, and progression of loss of visual acuity has been halted. Two months following the implant procedure, the regions of neovascularization have been diminished further, and the regions of edema have disappeared. The patient reports significantly restored visual acuity.

What is claimed is:

1. An ophthalmic composition comprising a therapeutic agent having enhanced effectiveness in the posterior segment of the eye, the composition comprising a bioactive agent covalently joined to a substrate of a membrane transporter, wherein the bioactive agent is brimonidine and the substrate of a membrane transporter is a dicarboxylate.

2. The composition of claim 1 which is formulated for topical administration.

3. The composition of claim 1 which is formulated as an intravitreal injectable.

4. The composition of claim 1 which is formulated as an intraocular implant.

5. The composition of claim 1 wherein said bioactive agent and said substrate are joined with a tissue labile bond.

* * * * *